(12) United States Patent
Powers et al.

(10) Patent No.: US 6,372,444 B1
(45) Date of Patent: Apr. 16, 2002

(54) SODD GENE EXPRESSION IN CANCER

(75) Inventors: Scott Powers, Greenlawn; Rong Wendy Zeng, Dix Hills, both of NY (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 09/417,559

(22) Filed: Oct. 13, 1999

(51) Int. Cl.$^7$ .................. G01N 33/574; G01N 33/53; G01N 33/48; C12Q 1/68; A61K 49/00
(52) U.S. Cl. ................... 435/7.23; 435/6; 435/4; 435/7.1; 435/7.2; 436/64; 424/9.1
(58) Field of Search .................... 435/7.1, 7.2, 7.23, 435/4, 6; 436/64; 424/9.1

(56) References Cited

U.S. PATENT DOCUMENTS 5,912,143 A * 6/1999 Bandman et al.
6,107,088 A * 8/2000 Korneluk et al.

OTHER PUBLICATIONS

Gallo et al. Int. J. Cancer (Pred. Oncol.) 84, 573–579 (1999).*

* cited by examiner

Primary Examiner—Anthony C. Caputa
Assistant Examiner—Gary B. Nickol
(74) Attorney, Agent, or Firm—Richard Aron Osman

(57) ABSTRACT

The invention provides methods and compositions for diagnosing and treating tumors. In particular embodiments, the invention provides methods for characterizing tumors for SODD gene copy number and/or expression and for using this diagnosis in guiding treatment options. Accordingly, the invention provides methods for biasing therapeutic options by (a) contacting a biopsy of a tumor with an agent which specifically binds a SODD gene or SODD gene product thereof; (b) measuring specific binding of the agent to the SODD gene or gene product to determine an amount of the SODD gene or gene product present in the biopsy; and (c) biasing therapeutic options for treating the tumor based on the amount of the SODD gene or gene product present in the biopsy.

17 Claims, No Drawings

SODD GENE EXPRESSION IN CANCER

FIELD OF THE INVENTION

The field of the invention is characterizing tumors by SODD gene copy number and/or expression.

BACKGROUND OF THE INVENTION

The discovery of cancer genes that correspond to the primary genetic alterations driving cancer cell growth and progression can have direct diagnostic and prognostic significance. A clear example of this is in childhood leukemia, where the design of effective therapeutic strategies became dependent upon an accurate molecular diagnosis of translocated cancer genes, once robust tools were developed to examine translocation of cancer genes in clinical samples of childhood leukemias (Table 1).

TABLE 1

Therapeutic implications of the molecular detection of translocated cancer genes.

| Translocation | Leukemia subtype | Recommended treatment |
| --- | --- | --- |
| TEL-AML | Pro-B cell | Antimetabolites |
| a | Pre-B cell | Genotoxic drugs and antimetabolites |
| Ig-MYC | B-cell | Genotoxic drugs and antimetabolites |
| BCR-ABL | Pro-B cell | Allogeneic stem cell transplantation |
| AML1-ETO | Myeloid-M2 | Intensive chemotherapy (cytarabine) |
| CBFβ-MYH11 | Myeloid-M4 | Intensive chemotherapy (cytarabine) |
| PML-RARa | Myeloid-M3 | Retinoic acid and chemotherapy |

In solid tumors such as breast cancer, two of the most promising prognostic markers are the p53 and HER2 cancer genes, both of which underlie common primary genetic alterations (Kovach et al., 1996, Proc. Natl. Acad. Sci. USA 93, 1093–1096; Hartmann et al., 1997, Trends Genet. 13, 27–33; Thor et al., 1998, J. Natl. Cancer Inst. 90, 1346–1360; Ross and Fletcher, 1998, Oncologist 3, 237–252), however it would be useful to develop more prognostic markers that correspond to primary genetic alterations.

Gene amplification is one of the primary mutational mechanisms for causing primary genetic alterations in solid tumors, and most of the chromosomal regions that undergo amplification are not well characterized and do not harbor known oncogenes. Discovery of these amplified cancer genes will provide novel targets for diagnostic development. Over 20 high-level amplified regions in breast cancers have been identified by CGH, but only three have been firmly associated with established oncogenes (HER2 at 17q12–q21, MYC at 8q24, and BCL1/Cyclin D1 at 11q13) (Knuutila et al., 1998, Am. J. Pathol. 152, 1107–1123).

By representational difference analysis (RDA) (Lisitsyn et al. 1995, Proc. Natl. Acad. Sci. USA 92, 151–155) of a human breast cancer biopsy, we discovered a RDA probe that mapped to 8p11 and that detected amplification in several breast cancer samples. Amplification of 8p11 is associated with amplification of FGFR1, although not all tumors amplified for FGFR1 overexpress the gene (Dib et al., 1995, Oncogene 10, 995–1001; Ugoline et al., 1999, Oncogene, 18, 1903–1910). Our results indicate that FGFR1 is not the only oncogene that is driving amplification of this region. For one, the cell line BT483 is not amplified for FGFR1 but amplified for the RDA probe. Second, one tumor (89-249) analyzed by quantitative RT-PCR did not have the FGFR1 gene overexpressed, which rules out FGFR1 as the oncogene responsible for amplification of the region in this tumor. Third, the physical map of this region revealed FGFR1 is ~0.6 Mb away from the RDA probe and there are sequences in between the RDA probe and FGFR1 that are not amplified or less amplified than the RDA probe and FGFR1. Thus the region amplified near the RDA probe contains a separate oncogene.

Based on more detailed analysis of these primary tumors, and analysis of additional amplified primary tumors, the smallest area of common overlap of amplification encompasses inter alia, SODD (originally coined from the acronym of "Suppressor of Death Domains"), a protein that binds to the TNF-receptor's death domain and that inhibits TNF-induced apoptosis (Jiang et al., 1999, Science 283, 543–546 and copending application Ser. No. 09/035,676, filed: Mar. 05, 1998).

SUMMARY OF THE INVENTION

The invention provides methods and compositions for diagnosing and treating tumors. In particular embodiments, the invention provides methods for characterizing tumors for SODD gene copy number and/or expression and for using this diagnosis in guiding treatment options. Accordingly, the invention provides methods for biasing therapeutic options by (a) contacting a biopsy of a tumor with an agent which specifically binds a SODD gene or SODD gene product thereof; (b) measuring specific binding of the agent to the SODD gene or gene product to determine an amount of the SODD gene or gene product present in the biopsy; and (c) biasing therapeutic options for treating the tumor based on the amount of the SODD gene or gene product present in the biopsy. The target may be a SODD gene, transcript (e.g. mRNA or cDNA), or translate (i.e. SODD polypeptide). SODD genes and transcripts are generally detected with specific hybridization probes, including PCR primers and translates are generally detected with SODD protein-specific binding agents, including SODD binding proteins like antibodies and TNF receptor domains. The amount of SODD gene or gene expression product in the tumor biopsy is used to guide treatment. For example, a relatively elevated amount of the SODD gene or gene product present in the biopsy can reduce the indicability or advisability of radiation therapy for treating the tumor.

DETAILED DESCRIPTION OF SPECIFIC EMBODIMENTS OF THE INVENTION

The present invention is based on the discovery that a diagnosis or prognosis of cancer can be determined by detecting elevated levels of SODD polypeptide or polynucleotides in a biological sample taken from an animal. As described below, any of a number of methods to detect the presence and/or levels of SODD can be used. A SODD polynucleotide level can be detected by detecting the presence of any SODD DNA or RNA, including SODD genomic DNA, mRNA, and cDNA. A SODD polypeptide can be detected by detecting a SODD polypeptide itself, or by detecting SODD protein activity, e.g., DNA or protein binding activity, transcription regulation, etc. Detection can involve quantification of the level of SODD (e.g., gDNA, cDNA, mRNA, protein, or protein activity), or, alternatively, can be a qualitative assessment of the level, or of the presence or absence, of SODD, in particular in comparison with a control level. Any of a number of methods to detect any of the above can be used, as described infra. Such methods include, for example, hybridization, amplification, and other assays.

The general methods involve (a) contacting a biopsy of a tumor with an agent under conditions wherein the agent specifically binds a SODD gene or SODD gene product thereof; (b) measuring specific binding of the agent to the SODD gene or gene product to determine an amount of the SODD gene or gene product present in the biopsy; and (c) biasing therapeutic options for treating the tumor based on the amount of the SODD gene or gene product present in the biopsy.

In certain embodiments, a level of SODD in a biological sample will be compared with a control sample taken from a cancer-free animal, or, preferably, with a value expected for a sample taken from a cancer-free animal. In a particularly preferred embodiment, an assay will be performed under conditions where only a higher than normal amount of SODD polynucleotide or polypeptide will be detectable in the assay. As a result, an elevated level of SODD can be detected in a sample using a simple assay giving a simple, positive or negative result, with no need for quantification of SODD levels or a direct comparison with a control sample.

In certain embodiments, the level of SODD polynucleotide, polypeptide, or protein activity will be quantified. In such embodiments, the difference between an elevated level of SODD and a normal, control level will preferably be statistically significant. In preferred embodiments, an elevated level of SODD polynucleotide, polypeptide, and/or protein activity will be at least about 2, 5, 10, or more fold greater than a control level.

Providing a Biological Sample. Essentially any sampleable tumor may be screened, including solid tumors such as breast cancers, blood borne tumors such as leukemias, etc. For example, using TaqMan quantitative RT-PCR analysis and SODD transcript specific primers, we have found SODD expression in breast tumor biopsies over 10-fold above that of normal human mammary gland tissue. The tumor biopsy or sample may take any convenient form, depending largely on the nature of the tumor, including a section of a solid mass, a fluid sample, a cellular or non-cellular extract or modified or unmodified fraction, etc. For example, in one embodiment, the biopsy comprises a nucleic acid fraction of a tumor portion.

The level and/or presence of SODD polynucleotides or polypeptides will be detected in a biological sample. A "biological sample" refers to a cell or population of cells or a quantity of tissue or fluid from an animal. Most often, the sample has been removed from an animal, but the term "biological sample" can also refer to cells or tissue analyzed in vivo, i.e., without removal from the animal. Typically, a "biological sample" will contain cells from the animal, but the term can also refer to non-cellular biological material, such as non-cellular fractions of blood, saliva, or urine, that can be used to measure SODD levels. Numerous types of biological samples can be used in the present invention, including a tissue biopsy, blood sample, a buccal scrape, a saliva sample, a nipple discharge, etc.

As used herein, a "tissue biopsy" refers to an amount of tissue removed from an animal for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc. A "buccal scrape" refers to a sample of cells removed from the inner lining of the mouth. A "nipple discharge" refers to fluid originating from a nipple, which may contain cancerous cells or may contain elevated levels of SODD polypeptide indicating the presence of cancerous cells in the breast.

SODD Detection. A wide variety of agents and binding measuring techniques may be used depending on the targeted SODD component. In one embodiment, the presence of cancer is evaluated simply by determining the copy number of SODD genes. The "copy number of SODD genes" refers to the number of DNA sequences in a cell encoding a SODD protein. Generally, for a given autosomal gene, an animal has two copies of each gene. The copy number can be increased, however, by gene amplification or duplication, e.g., in cancer cells, or reduced by deletion. Methods of evaluating the copy number of a particular gene are well known to those of skill in the art, and include, inter alia, hybridization and amplification based assays.

Hybridization-based Assays. Any of a number of hybridization based assays can be used to detect the copy number of SODD genes in the cells of a biological sample. One such method is by Southern Blot. In a Southern Blot, genomic DNA is typically, fragmented, separated electrophoretically, and hybridized to a SODD specific probe. Comparison of the intensity of the hybridization signal from the probe for the target region with control probe signal from analysis of normal genomic DNA (e.g., a non-amplified portion of the same or related cell, tissue, organ, etc.) provides an estimate of the relative SODD copy number.

An alternative means for determining the copy number of SODD genes in a sample is in situ hybridization, e.g., fluorescence in situ hybridization, or FISH. In situ hybridization assays are well known (e.g., Angerer (1987) Meth. Enzymol 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments.

The probes used in such applications are typically labeled, e.g., with radioisotopes or fluorescent reporters. Preferred probes are sufficiently long, e.g., from about 50, 100, or 200 nucleotides to about 1000 or more nucleotides, so as to specifically hybridize with the target nucleic acid(s) under stringent conditions.

In preferred embodiments, "comparative probe" methods, such as comparative genomic hybridization (CGH), are used to detect SODD gene amplification. In comparative genomic hybridization methods, a "test" collection of nucleic acids is labeled with a first label, while a second collection (e.g., from a healthy cell or tissue) is labeled with a second label. The ratio of hybridization of the nucleic acids is determined by the ratio of the first and second labels binding to each fiber in the array. Differences in the ratio of the signals from the two labels, e.g., due to gene amplification in the test collection, is detected and the ratio provides a measure of the SODD gene copy number.

Hybridization protocols suitable for use with the methods of the invention are described, e.g., in Albertson (1984) EMBO J. 3: 1227–1234; Pinkel (1988) Proc. Natl. Acad. Sci. USA 85: 9138–9142; EPO Pub. No. 430,402; Methods in Molecular Biology, Vol. 33. In Situ Hybridization Protocols, Choo, ed., Humana Press, Totowa, N.J. (1994), etc.

Amplification-based Assays. In still another embodiment, amplification-based assays are used to measure a SODD copy number. In such assays, the SODD nucleic acid sequences act as a template in an amplification reaction (e.g. PCR). In a quantitative amplification, the amount of amplification product will be proportional to the amount of template in the original sample. Comparison to appropriate controls provides a measure of the copy number of the SODD gene. Methods of quantitative amplification are well known to those of skill in the art. Detailed protocols for quantitative PCR are provided, e.g., in Innis et al. (1990) PCR Protocols, A Guide to Methods and Applications, Academic Press, Inc. N.Y.). The known nucleic acid sequence for SODD (see, e.g., Jiang et al, 1999, supra) is sufficient to enable one of skill to routinely select primers to amplify any portion of the gene.

In preferred embodiments, a TaqMan based assay is used to quantify SODD polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer, e.g., www2. perkin-elmer.com).

Other suitable amplification methods include, but are not limited to, ligase chain reaction (LCR) (see, Wu and Wallace (1989) *Genomics* 4:560, Landegren et al. (1988) *Science* 241:1077, and Barringer et al. (1990) *Gene* 89:117), transcription amplification (Kwoh et al. (1989) *Proc. Natl. Acad. Sci. USA* 86:1173), self-sustained sequence replication (Guatelli et al. (1990) *Proc. Nat. Acad. Sci. USA* 87:1874), dot PCR, and linker adapter PCR, etc.

Detection of Gene TranscriptDirect hybridization-based assays. Methods of detecting and/or quantifying the level of SODD gene transcript (SODD mRNA or cDNA made therefrom) using nucleic acid hybridization techniques are known to those of skill in the art (see, Sambrook el al., (1989) *Molecular Cloning: A Laboratory Manual*, 2d Ed., vols 1–3, Cold Spring Harbor Press, New York).

For example, one method for evaluating the presence, absence, or quantity of SODD cDNA involves a Southern Blot as described above. Briefly, SODD mRNA is isolated using standard methods and reverse transcribed to produce cDNA. The cDNA is then optionally digested, run on a gel, and transferred to a membrane. Hybridization is then carried out using nucleic acid probes specific for SODD cDNA and detected using standard techniques (see, e.g., Sambrook et al., supra).

Similarly, a Northern transfer may be used to detect an mRNA directly. In brief, in a typical embodiment, mRNA is isolated from a given biological sample, electrophoresed to separate the mRNA species, and transferred from the gel to a nitrocellulose membrane. As with the Southern Blots, labeled SODD probes are used to identify and/or quantify the mRNA.

Amplification-based assays. In another preferred embodiment, a SODD transcript (e.g., SODD mRNA) can be measured using amplification-based methods (e.g., PCR). In a preferred embodiment, a transcript level is assessed by using reverse transcription PCR (RT-PCR). RT-PCR methods are well known to those of skill in the art (see, e.g., Ausubel et al., supra).

Accordingly, where the targeted SODD component is a SODD gene or transcript, the agent generally comprises a specific hybridization probe or primer. Any convenient method for measuring hybridization may be used, including radiolabel detection (e.g. in in situ hybridizations, Northern or Southern blots), fluorescent polarization assays, quenching assays, PCR product assays, etc. For example, Table 2 shows exemplary SODD-specific hybridization probes used to detect SODD transcripts in situ and in PCR reactions.

TABLE 2

Exemplary SODD-specific hybridization probes and PCR primers

| Probe | SODD-specific hybridization in in situ hybridization | SODD-specific detection of PCR amplified SODD transcripts |
|---|---|---|
| #pT012 | ++++ | ++++ |
| #pT047 | ++++ | ++++ |
| #pT053 | ++++ | ++++ |
| #pT058 | ++++ | ++++ |
| #pT069 | ++++ | ++++ |
| #pT103 | +++ | ++++ |

Detection of Expressed Protein. SODD levels can also be detected and/or quantified by detecting or quantifying SODD polypeptide. SODD polypeptide can be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In a preferred embodiment, a SODD polypeptide is detected using an immunoassay such as an ELISA assay (see, e.g., Crowther, John R. *ELISA Theory and Practice.* Humana Press: New Jersey, 1995). As used herein, an "immunoassay" is an assay that utilizes an antibody to specifically bind to the analyte (i.e., the SODD polypeptide). The immunoassay is thus characterized by detection of specific binding of a SODD polypeptide to an anti-SODD antibody.

In an immunoassay, SODD polypeptide can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 377: *Antibodies in Cell Biology*, Academic Press, Inc. New York; Stites & Terr (1991) *Basic and Clinical Immunology* 7th Edition.

Immunoassays typically rely on direct or indirect labeling methods to detect antibody-analyte binding. For example, an anti-SODD antibody can be directly labeled, thereby allowing detection. Alternatively, the anti-SODD antibody may itself be unlabeled, but may, in turn, be bound by a labeled third antibody specific to antibodies of the species from which the second antibody is derived. The second or third antibodies can also be modified with a detectable moiety, e.g., as biotin, to which a third labeled molecule can specifically bind, such as enzyme-labeled streptavidin. Also, other antibody-binding molecules can be used, e.g., labeled protein A or G (see, generally Kronval, et al. (1973) *J. Immunol.*, 111:1401–1406, and Akerstrom (1985) *J Immunol.*, 135:2589–2542).

Immunoassays for detecting a SODD polypeptide can be competitive or noncompetitive. Noncompetitive immunoassays are assays in which the amount of captured analyte is directly measured. In a preferred embodiment, "sandwich" assays will be used, for example, wherein anti-SODD antibodies are bound directly to a solid substrate where they are immobilized. These immobilized antibodies then capture the SODD protein present in a test sample. The SODD thus immobilized is then bound by a labeling agent, such as a second anti-SODD antibody bearing a label. In competitive assays, the amount of SODD protein present in a sample is measured indirectly, e.g., by measuring the amount of added (exogenous) SODD displaced (or competed away) from an anti SODD antibody by SODD protein present in a sample. For example, a known amount of labeled SODD polypeptide is added to a sample and the sample is then contacted with an anti-SODD antibody. The amount of labeled SODD polypeptide bound to the antibody is inversely proportional to the concentration of SODD polypeptide present in the sample.

Any of a number of labels can be used in any of the immunoassays of this invention, including fluorescent labels, radioisotope labels, or enzyme-based labels, wherein a detectable product of enzyme activity is detected (e.g., peroxidase, alkaline phosphatase, β-galactosidase, etc.). Antibodies for use in the various immunoassays described herein can be produced according to standard methods (see, e.g., Harlow and Lane (1988) *Antibodies: A Laboratory Manual*, Cold Spring Harbor Press, N.Y.)

Detection of SODD Protein Activity. In another embodiment, SODD polypeptide levels are determined by virtue of the SODD protein activity in a biological sample. Such protein activity can be easily measured using standard techniques, see e.g. Jiang et al., 1999, supra.

Accordingly, where the targeted SODD component is a SODD gene translate (polypeptide), the agent comprises a SODD-specific binding moiety such as that of a natural intracellular SODD binding target (e.g. TNF-R1), mutant thereof (e.g. TNF-R1Δ407–426; TNF-R1Δ212–308; see Jiang et al. 1999, supra), a SODD regulating protein or other regulator that directly modulates SODD activity or its localization, a non-natural SODD binding target (e.g. a specific immune protein such as an antibody, T-cell receptor, or antigen binding domain thereof) or an SODD specific agent such as those identified in screening assays such as described herein (see, TPS-1 Protocol for high throughput in vitro SODD-TNFR1 Death Domain binding assay, below). The SODD-specific binding moiety may be directly or indirectly labeled. For example, Table 3 shows SODD-specific antibodies made to a bacterially produced His-tagged SODD protein specifically identified SODD overexpression Western blot analyses of amplified breast cancer cells; in addition, immunohistochemical staining of amplified and non-amplified tumor samples with these antibodies revealed that tumor cells from amplified cases stained positively.

TABLE 3

SODD-specific antibodies tested by Western blot analyses of amplified breast cancer cells and by immunohistochemical staining of amplified and non-amplified tumor samples.

| Compound | SODD-specific detection in Western blot analysis | SODD-specific detection by immunohistochemical analysis. |
|---|---|---|
| #SAb002 | ++++ | ++++ |
| #SAb039 | ++++ | +++ |
| #SAb083 | ++++ | ++++ |
| #SAb127 | ++++ | ++++ |
| #SAb149 | ++++ | +++ |
| #SAb344 | ++++ | ++++ |

As additional examples, Table 4 shows shows small (>500 Da) molecule SODD specific binding agents identified in the TPS-1 binding interference protocol (details below).

TABLE 4

Exemplary mall MW SODD-specific binding agents identified in TPS-1 assay.

| Compound | SODD-TNFR1 Death Domain in vitro binding interference assay (TPS-1 protocol) | SODD detection w $^3$H-radiolabeled compound in situ |
|---|---|---|
| #PW012 | ++++ | ++++ |
| #PW047 | ++++ | + |
| #PW053 | +++ | ++++ |
| #PW058 | +++ | ++++ |
| #PW069 | ++++ | ++ |
| #PW103 | ++ | ++++ |

Diagnosing Cancer. The present invention provides numerous methods for diagnosing any of a number of types of cancer, e.g., determining whether or not an animal has a cancer, whether or not a biological sample contains cancerous cells, estimating the likelihood of the animal developing cancer, and monitoring the efficacy of anti-cancer treatment in an animal with cancer. Such methods are based on the surprising result that cancer cells have an elevated level of SODD polynucleotide (i.e., gene copy number and/or mRNA) and polypeptide level. Further, the presence of cancerous cells can be determined indirectly, i.e., in certain embodiments a biological sample that does not itself contain cancerous cells, but which has been taken from an animal with cancerous cells elsewhere in its body, may contain elevated levels of SODD reflecting the presence of the cancerous cells.

Detecting a Cancer. In numerous embodiments of the present invention, the level and/or presence of SODD polynucleotide or polypeptide will be detected in a biological sample, thereby detecting the presence or absence of cancerous cells in the biological sample, or, in certain embodiments, in the animal from which the biological sample was removed. In preferred embodiments, the biological sample will comprise a tissue sample from a tissue suspected of containing cancerous cells. Often, such methods will be used in conjunction with additional diagnostic methods, e.g., detection of other cancer markers, mammography, etc. In other embodiments, a tissue sample known to contain cancerous cells, e.g., from a tumor, will be detected for SODD levels to determine information about the cancer, e.g., the efficacy of certain treatments, the survival expectancy of the animal, etc.

The amount of SODD polynucleotide or polypeptide used to determine the presence of a cancer will depend on numerous factors, including the type of cancer, the age, sex, medical history, etc., of the patient, the cell type, the assay format, etc. In preferred embodiments, a level of SODD in a biological sample will not be quantified or directly compared with a control sample, but will rather be detected relative to a "diagnostic presence" of SODD, wherein a "diagnostic presence" refers to the amount of SODD polynucleotide or polypeptide that indicates the presence of cancer, or the likelihood of cancer, in a particular sample. Preferably, a "diagnostic presence" will be detectable in a simple assay giving a positive or negative result, where a positive "detection" of a "diagnostic presence" of SODD polynucleotide or polypeptide indicates the presence of cancer in the animal.

The SODD level need not be quantified for a "diagnostic presence" to be detected, merely any method of determining whether SODD is present at levels higher than in a normal, cancer free cell, sample, or animal. In addition, a "diagnostic presence" does not refer to any absolute quantity of SODD, but rather to an amount that, depending on the biological sample, cell type, assay conditions, medical condition, etc., is sufficient to distinguish the level in a cancerous, or pre-cancerous sample, from a normal, cancer-free sample.

Such methods can be practiced regardless of whether any SODD polynucleotide or polypeptide is normally present, or "expected" to be present, in a particular control sample. For example, SODD may not be expressed in certain cell types, resulting in a complete absence of SODD in a control biological sample consisting of such cell types. For such biological sample, a "diagnostic presence" refers to any detectable amount of SODD. In other tissues, however, there may be a detectable level of SODD present in normal, cancer-free cells, and a "diagnostic presence" represents a level that is higher than the normal level, preferably representing a "statistically significant" increase over the normal level. Often, a "diagnostic presence" of SODD polynucleotide, polypeptide, and/or protein activity in a biological sample will be at least about 2, 5, 10, or more fold greater than a level expected in a sample taken from a normal, cancer-free animal.

Further, the present methods can be used to assess the efficacy of a course of treatment. For example, in an animal from which a biological sample has been found to contain an elevated amount of SODD polynucleotide or polypeptide, which elevated amount of SODD polynucleotide or polypeptide indicated the application of an anti-cancer therapy to the animal, the efficacy of the treatment can be assessed by monitoring, over time, SODD levels. For example, a reduction in SODD polynucleotide or polypeptide levels in a biological sample taken from an animal following a treatment, compared to a level in a sample taken from the animal before the treatment, indicates efficacious treatment.

Determining a Prognosis. The level of SODD can be used to determine the prognosis of an animal with a cancer. For example, if a cancer is detected using a technique other than by detecting SODD, e.g., tissue biopsy, then the presence or absence of SODD can be used to determine the prognosis for the animal with the cancer. For example, an animal with a cancer that has elevated levels of SODD may have a reduced survival expectancy compared to an animal with a cancer, but which has normal levels of SODD, where "survival expectancy" refers to a prediction regarding the severity, duration, or progress of a disease, condition, or any symptom thereof. Methods of correlating SODD levels, or the presence or absence of SODD, with a survival expectancy, likelihood of recurrence of a cancer, and other prognostic factors are well known and can be readily practiced. In addition, alternative prognostic indicators, e.g., the level or presence of other marker levels, can also be detected.

Determining a Preferred Course of Treatment. The present methods can be used to determine the optimal course of treatment in an animal with cancer. For example, the presence or absence of an elevated level of SODD can indicate the survival expectancy of an animal with a cancer, thereby indicating a more or less aggressive treatment for the animal. In addition, a correlation can readily be established between levels of SODD, or the presence or absence of an elevated level of SODD, and the relative efficacy of one or another anti-cancer agent. Such analyses can be performed, e.g., retrospectively, i.e., by detecting SODD levels in samples taken previously from animals that have subsequently undergone one or more types of anti-cancer therapy, and correlating the SODD levels with the known efficacy of the treatment.

In particular, SODD expression is shown to affect tumor cell response to particular treatments. SODD overexpression blocks,TNF-induced apoptosis (Jiang et al., 1999, supra), and the TNF-signaling pathway is known to help mediate apoptosis induced by certain standard cancer treatments such as irradiation (Sheikh et al., 1998, Oncogene 17, 2555–2563; Zhuang et al., 1999, J. Immunol. 162, 1440–1447) and taxanes (Lanni et al., 1999, J. Biol. Chem. 274, 13451–13455); see also Lee et al., 1997, Proc. Natl. Acad. Sci. USA 94, 9679–9683). Accordingly, once the amount of the SODD gene or gene product in the biopsy is determined, this measurement is used to bias the therapeutic options for treating the tumor. In a particular embodiment, this method determines a relatively elevated amount of the SODD gene or gene product present in the biopsy and the biasing step comprises reducing the indicability (advisability) of therapies which are mediated at least in part by TNF signaling induced apoptosis, e.g. radiation therapy, for treating the tumor.

Treating cancer. The present invention provides numerous methods for treating an animal with a cancer. In addition to allowing the determination of an optimal treatment for an animal with cancer, as described supra, methods are provided for treating a cancer by inhibiting the growth and/or proliferation of a cancer cell. As used herein, such methods are directed at reducing the level of SODD polypeptides, polynucleotides, or protein activity in a cancerous cell. It will be appreciated that more than one of the methods described infra can be performed on a given animal, and may also be administered in conjunction with one or more traditional, well known anti-cancer therapies, e.g., chemotherapy, radiation therapy, surgery, hormone therapy, immunotherapy, etc.

According to the present invention, a "method of treating cancer" refers to a procedure or course of action that is designed to reduce or eliminate the number of cancer cells in an animal, or to alleviate the symptoms of a cancer. "A method of treating cancer" does not necessarily mean that the cancer cells will, in fact, be eliminated, that the number of cells will, in fact, be reduced, or that the symptoms of a cancer will, in fact, be alleviated. Often, a method of treating cancer will be performed even with a low likelihood of success, but which, given the medical history and estimated survival expectancy of an animal, is deemed an overall beneficial course of action.

In certain embodiments, the present invention provides methods for treating cancer by detecting the level and/or a diagnostic presence of SODD polynucleotide or polypeptide in a biological sample, and, when a diagnostic presence is detected, applying one or more of the above-listed anti-cancer therapies.

One commonly applied anti-cancer therapy is chemotherapy. As used herein, "chemotherapy" refers to the administration of chemical compounds to an animal with cancer that is aimed at killing or reducing the number of cancer cells within the animal. Generally, chemotherapeutic agents arrest the growth of or kill cells that are dividing or growing, such as cancer cells. Examples of chemotherapeutic agents include doxirubicin, vinblastine, genistein, taxol, vincristine, etc.

Another commonly applied anti-cancer therapy is radiation therapy. "Radiation therapy" refers to the administration of radioactivity to an animal with cancer. Radiation kills or inhibits the growth of dividing cells, such as cancer cells. The administration of radiation may be from an external source (e.g., a gammua source, a proton source, a molecular beam source, etc.), or may be through an implantable radioactive material.

In numerous embodiments, a tissue found to be cancerous using the present methods will be removed using surgery. "Surgery" refers to the direct removal or ablation of cells, e.g., cancer cells, from an animal. Most often, the cancer cells will be in the form of a tumor (e.g., a mammary tumor), which is removed from the animal. The surgical methods may involve removal of healthy as well as cancerous tissue.

Hormone therapy can also be used to treat cancers, e.g., breast cancer. As used herein, "hormone therapy" refers to the administration of compounds that counteract or inhibit hormones, such as estrogen or androgen, that have a mitogenic effect on cells. Often, such hormones act to increase the cancerous properties of cancer cells in vivo. "Hormone therapy" can also include methods of reducing or eliminating the production of hormones in an animal, e.g., the surgical removal of ovaries in an animal to prevent estrogen production. In certain embodiments, immunotherapy will be used to treat a cancer, e.g., a cancer detected using the present methods. "Immunotherapy" refers to methods of enhancing the ability of an animal's immune system to destroy cancer cells within the animal. Numerous such methods are well known to those of skill in the art. This can involve the treatment with polyclonal or monoclonal antibodies (e.g., Herceptin) that bind to particular molecules located on, produced by, or indicative of, tumor cells. Immunotherapeutic methods are well know to those of skill in the art (see, e.g., Pastan et al.(1992) *Ann. Rev. Biochem.*, 61:331–354, Brinkman and Pastan (1994) *Biochimica BiphysicaActa*, 1198:27–45, etc.).

Reducing SODD Activity Levels in Cells. In preferred embodiments, this invention provides methods of treating a cancer by reducing SODD levels in a cell. Typically, such methods are used to reduce an elevated level of SODD, e.g., an elevated level in a cancerous cell. According to the present invention, "reducing the level of SODD activity" refers to inhibiting SODD protein activity in the cell, lowering the copy number of SODD genes, or decreasing the level of SODD mRNA or protein in the cell. Preferably, the level of SODD activity is lowered to the level typical of a normal, cancer-free cell, but the level may be reduced to any level that is sufficient to decrease the proliferation of the cell, including to levels below those typical of normal cells. Preferably, such methods involve the use of inhibitors of SODD, where an "inhibitor of SODD" is a molecule that acts to reduce SODD polynucleotide levels, SODD polypeptide levels and/or SODD protein activity. Such an inhibitor can include antisense polynucleotides, ribozymes, antibodies, dominant negative SODD forms, and small molecule inhibitors of SODD.

In preferred embodiments, SODD levels will be reduced so as to reduce the proliferation of a cancer cell with elevated SODD levels. The "proliferation" of a cell refers to the rate at which the cell or population of cells grows and divides, or to the extent to which the cell or population of cells grows, divides or increases in number. "Proliferation" can reflect multiple factors, including the rate of cell growth and division and the rate of cell death. A method of "decreasing" the proliferation of a cell means to reduce the rate or extent of growth or division of a cell or population of cells. Such methods can involve preventing cell division or cell growth, and may also include cell killing, and can be practiced in vivo or in vitro.

In preferred embodiments, SODD levels will be reduced in a tumor cell, a hyperproliferative cell, and/or a metastatic cell. A "tumor cell" is a cancer cell, in vitro or in vivo, that is part of a tumor, has been isolated from a tumor, or which is capable of forming a tumor. A "hyperproliferative cell" is a cell with an abnormally high rate of proliferation, or a cell that proliferates to an abnormally great extent, i.e., gives rise to a population of cells that increases in number over time. Typically, cancer cells are metastatic, i.e., capable of leaving their normal anatomical location and moving to, and proliferating in, another part of an animal. Typically, such "metastatic" cells have acquired the ability to cross basal laminae so as to leave their normal tissue, enter the circulation, leave the circulation, and proliferate in a new location.

Antisense Polynucleotides. In certain embodiments, SODD activity is downregulated, or entirely inhibited, by the use of antisense polynucleotides. An "antisense polynucleotide" is a nucleic acid complementary to, and which can preferably hybridize specifically to, a coding mRNA nucleic acid sequence, e.g, SODD mRNA, or a subsequence thereof. Binding of the antisense polynucleotide to the SODD mRNA reduces the translation and/or stability of the SODD mRNA. In the context of this invention, antisense polynucleotides can comprise naturally-occurring nucleotides, or synthetic species formed from naturally-occurring subunits or their close homologs. Antisense polynucleotides may also have altered sugar moieties or inter-sugar linkages. Exemplary among these are the phosphorothioate and other sulfur containing species which are known for use in the art. All such analogs are comprehended by this invention so long as they function effectively to hybridize with SODD mRNA. Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Ribozymes. In addition to antisense polynucleotides, ribozymes can be used to target and inhibit transcription of SODD. A ribozyme is an RNA molecule that catalytically cleaves other RNA molecules. Different kinds of ribozymes have been described, including group I ribozymes, hammerhead ribozymes, hairpin ribozymes, RNAse P, and axhead ribozymes (see Castanotto et al. (1994) *Adv. in Pharmacology* 25:289–317 for a general review of the properties of different ribozymes). The general features of hairpin ribozymes are described, e.g., in Hampel et al. (1990) *Nucl. Acids Res*. 18:299–304; Hampel et al. (1990) European Patent Publication No. 0 360 257; U.S. Pat. No. 5,254,678. Methods of preparing are well known to those of skill in the art (see, e.g., Wong-Staal et al., WO 94/26877; Ojwang et al. (1993) *Proc. Natl. Acad. Sci. USA* 90:6340–6344; Yamada et al. (1994) *Human Gene Therapy* 1:39–45; Leavitt et al. (1995) *Proc. Natl. Acad. Sci. USA* 92:699–703; Leavitt et al. (1994) *Human Gene Therapy* 5:1151–120; and Yamada et al. (1994) *Virology* 205:121–126).

Inhibitors of SODD Polypeptide Activity. SODD activity can also be decreased by the addition of an inhibitor of the SODD polypeptide. This can be accomplished in any of a number of ways, including by providing a dominant negative SODD polypeptide, e.g., a form of SODD that itself has no activity and which, when present in the same cell as a functional SODD, reduces or eliminates the SODD activity of the functional SODD. Also, inactive polypeptide variants (muteins) can be used, e.g., by screening for the ability to inhibit SODD activity. Methods of making muteins are well known to those of skill (see, e.g., U.S. Pat. Nos. 5,486,463, 5,422,260, 5,116,943, 4,752,585, 4,518,504).

Screening for SODD Inhibitors. In one embodiment, this invention provides methods of screening for agents that modulate and preferably downregulate SODD protein activity. Preferred "screening" methods of this invention involve (i) contacting a SODD-expressing cell (e.g., a cell capable of expressing SODD) with a test agent; and (ii) detecting the level of SODD activity (e.g., as described above), where a decreased level of SODD activity as compared to the level of SODD activity in a cell not contacted with the test agent indicates that the test agent inhibits or downregulates SODD.

Virtually any agent can be tested in such an assay. Such agents include, but are not limited to, natural or synthetic nucleic acids, natural or synthetic polypeptides, natural or synthetic lipids, natural or synthetic small organic molecules, and the like. In one preferred format, test agents are provided as members of a combinatorial library. In preferred embodiments, a collection of small molecule inhibitors are tested for SODD inhibiting ability. A "small molecule inhibitor" of SODD is any molecule, e.g., a carbohydrate, nucleotide, amino acid, oligonucleotide, oligopeptide, lipid, inorganic compound, etc. that inhibits SODD protein activity. Such molecules can inhibit SODD protein activity by any of a number of mechanisms, e.g., by binding to a SODD protein and competitively inhibiting its interaction with DNA or with other proteins. Preferably, such "small molecule inhibitors" are smaller than about 10 kD. More preferably, such inhibitors are smaller than about 5, 2, or 1 kD or even smaller. Test agents can also be screened based on functional properties of SODD protein, see, Jiang, et al., 1999, supra.

(i) Combinatorial Libraries. In certain embodiments, combinatorial libraries of potential SODD modulators will be screened for SODD-inhibiting ability. Conventionally, new chemical entities with useful properties are generated by identifying a chemical compound (called a "lead compound") with some desirable property or activity, e.g., SODD inhibiting activity, creating variants of the lead compound, and evaluating the property and activity of those variant compounds. Because of the ability to test large numbers quickly and efficiently, high throughput screening (HTS) methods are replacing conventional lead compound identification methods. In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et al. (1994)*J Med. Chem.* 37(9): 1233–1251).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J Pept. Prot. Res.*, 37: 487–493, Houghton et al. (1991) *Nature*, 354:84–88), peptoids (PCT Publication No WO 91/19735, 26 Dec. 1991), encoded peptides (PCT Publication WO 93/20242, 14 Oct. 1993), random biooligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90:6909–6913), vinylogous polypeptides (Hagihara et al. (1992) *J Amer. Chem. Soc.* 114:6568), nonpeptidal peptidomimetics with a Beta-D-Glucose scaffolding (Hirschmann et al., (1992) *J Amer. Chem. Soc.* 114:9217–9218), analogous organic syntheses of small compound libraries (Chen et al. (1994) *J Amer. Chem. Soc.* 116:2661), oligocarbamates (Cho, et al., (1993) *Science* 261:1303), and/or peptidyl phosphonates (Campbell et al., (1994) *J Org. Chem.* 59:658). See, generally, Gordon et al., (1994) *J Med. Chem.* 37:1385, nucleic acid libraries (see, e.g., Strategene, Corp.), peptide nucleic acid libraries (see, e.g., U.S. Pat. No. 5,539,083), antibody libraries (see, e.g., Vaughn et al. (1996) *Nature Biotechnology*, 14(3): 309–314), and PCT/US96/10287), carbohydrate libraries (see, e.g., Liang etal., (1996) *Science*, 274: 1520–1522, and U.S. Pat. No. 5,593,853), and small organic molecule libraries (see, e.g., benzodiazepines, Baum (1993) C&EN, January 18, page 33; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514; and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

(ii) High Throughput Screening. Any of the assays to identify compounds capable of modulating SODD levels described herein are amenable to high throughput screening. Preferred assays thus detect enhancement or inhibition of SODD gene transcription, inhibition or enhancement of SODD polypeptide expression, and inhibition or enhancement of SODD polypeptide activity. High throughput assays for the presence, absence, quantification, or other properties of particular nucleic acids or protein products are well known to those of skill in the art. Similarly, binding assays and reporter gene assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, OH; Beckman Instruments, Inc. Fullerton, Calif.; Precision Systems, Inc., Natick, Mass., etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

The TPS-1 Protocol for in vitro screening of agents which modulate SODD-TNFR1 Death Domain binding provides an exemplary high throughput screen:

TPS-1 Protocol for High Throughput In Vitro SODD-TNFR1 Death Domain Binding Assay.

A. Reagents:

Neutralite Avidin: 20 µg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM b-mercaptoethanol, 1 mg/ml BSA, cocktail of protease inhibitors.

$^{33}$P SODD polypeptide 10×stock: $10^{-8}$–$10^{-6}$M "cold" SODD supplemented with 200,000–250,000 cpm of labeled SODD (Beckman counter). Place in the 4° C. microfridge during screening.

Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVO_3$ (Sigma #S-6508) in 10 ml of PBS.

TNFR1 deletion mutant: $10^{-7}$–$10^{-5}$ M biotinylated TNFR1 80 residue death domain in PBS.

B. Preparation of Assay Plates:

Coat with 120 µl of stock N-Avidin per well overnight at 4° C.

Wash 2 times with 200 µl PBS.

Block with 150 µl of blocking buffer.

Wash 2 times with 200 µl PBS.

C. Assay:

Add 40 µl assay buffer/well.

Add 10 µl compound or extract.

Add 10 µl $^{33}$P-SODD (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 µM biotinylated TNFR1 deletion mutant (0.1–10 pmoles/40 ul in assay buffer)

Incubate 1 hour at room temperature.

Stop the reaction by washing 4 times with 200 µM PBS.

Add 150 µM scintillation cocktail.

Count in Topcount.

D. Controls for all Assays (Located on Each Plate):

a. Non-specific binding b. Soluble (non-biotinylated TNFR1 deletion mutant) at 80% inhibition.

Administration of SODD-inhibiting Compounds. In numerous embodiments of the present invention, a SODD inhibiting compounds, i.e., a compound that reduces levels of SODD mRNA, polypeptide and/or protein activity, will be administered to an animal. Such compounds can be administered by a variety of methods including, but not limited to, parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include, but are not limited to, powder, tablets, pills, capsules and lozenges. It is recognized that the SODD modulators (e.g., antibodies, antisense constructs, ribozymes, small organic molecules, etc.) when administered orally, must be protected from digestion. This is typically accomplished either by complexing the molecule(s) with a composition to render it resistant to acidic and enzymatic hydrolysis, or by packaging the molecule(s) in an appropriately resistant carrier, such as a liposome. Means of protecting agents from digestion are well known in the art.

The compositions for administration will commonly comprise a SODD modulator dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing modulators of SODD can be administered for therapeutic or prophylactic treatments. In therapeutic applications, compositions are administered to a patient suffering from a disease (e.g., a cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient.

Introducing Nucleic Acids into Cells. In numerous embodiments, one or more nucleic acids, e.g., SODD polynucleotides, such as antisense polynucleotides or ribozymes, will be introduced into cells, in vitro or in vivo. The present invention provides methods, reagents, vectors, and cells useful for expression of SODD and other polypeptides and nucleic acids using in vitro (cell-free), ex vivo or in vivo (cell or organism-based) recombinant expression systems.

The particular procedure used to introduce the nucleic acids into a host cell for expression of a protein or nucleic acid is application specific. Any of the well known procedures for introducing foreign nucleotide sequences into host cells may be used. These include the use of calcium phosphate transfection, spheroplasts, electroporation, liposomes, microinjection, plasma vectors, viral vectors and any of the other well known methods for introducing cloned genomic DNA, cDNA, synthetic DNA or other foreign genetic material into a host cell (see, e.g., Berger and Kimmel, *Guide to Molecular Cloning Techniques, Methods in Enzymology* volume 152 Academic Press, Inc., San Diego, Calif. (Berger), F. M. Ausubel et al., eds., Current Protocols, a joint venture between Greene Publishing Associates, Inc. and John Wiley & Sons, Inc., (supplemented through 1999), and Sambrook et al., *Molecular Cloning—A Laboratory Manual* (2nd Ed.), Vol. 1–3, Cold Spring Harbor Laboratory, Cold Spring Harbor, N.Y., 1989.

Vectors. In numerous embodiments of this invention, nucleic acids encoding SODD polypeptides, or inhibitors thereof, will be inserted into vectors using standard molecular biological techniques. Vectors may be used at multiple stages of the practice of the invention, e.g., for subcloning nucleic acids encoding SODD polypeptides or SODD inhibitors, e.g., SODD ribozymes or antisense sequences, or for subcloning additional elements used to control protein or mRNA expression, vector selectability, etc. Vectors may also be used to maintain or amplify the nucleic acids, for example, by inserting the vector into prokaryotic or eukaryotic cells and growing the cells in culture. In addition, vectors may be used to introduce and express SODD nucleic acids, or SODD-inhibiting nucleic acids, e.g., SODD ribozymes or antisense sequences, into cells for therapeutic or experimental purposes.

A variety of commercially or commonly available vectors and vector nucleic acids can be converted into a vector of the invention by cloning a polynucleotide of this invention into the commercially or commonly available vector. A variety of common vectors suitable for this purpose are well known in the art. For cloning in bacteria, common vectors include pBR322-derived vectors such as pBLUESCRIPT™, and bacteriophage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

Typically, a nucleic acid subsequence encoding a SODD polypeptide is placed under the control of a promoter. A nucleic acid is "operably linked" to a promoter when it is placed into a functional relationship with the promoter. For instance, a promoter or enhancer is operably linked to a coding sequence if it increases or otherwise regulates the transcription of the coding sequence. Similarly, a "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include promoters and, optionally, introns, polyadenylation signals, and transcription termination signals. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

An extremely wide variety of promoters are well known, and can be used in the vectors of the invention, depending on the particular application. Ordinarily, the promoter selected depends upon the cell in which the promoter is to be active. Other expression control sequences such as ribosome binding sites, transcription termination sites and the like are also optionally included. For *E. coli*, example control sequences include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, a retrovirus (e.g., an LTR based promoter) etc., and a polyadenylation sequence, and may include splice donor and acceptor sequences.

Cancers. The present methods can be used to diagnose and treat any of a number of types of cancers. In preferred embodiments, epithelial cancers will be diagnosed and/or treated. For example, breast, ovarian, colorectal, kidney, stomach, bladder, lung, and any other epithelial cancer can be treated or diagnosed. In addition, a cancer at any stage of progression can be detected, such as primary, metastatic, and recurrent cancers. Information regarding numerous types of cancer can be found, e.g., from the American Cancer Society (www3.cancer.org), or from, e.g., Wilson et al. (1991) Harrison's Principles of Internal Medicine, $12^{th}$ Edition, McGraw-Hill, Inc.

Kits for Use in Diagnostic and/or Prognostic Applications. For use in diagnostic, research, and therapeutic applications suggested above, kits are also provided by the invention. In the diagnostic and research applications such kits may include any or all of the following: assay reagents, buffers, SODD specific nucleic acids or antibodies, hybridization probes and/or primers, antisense polynucleotides, ribozymes, dominant negative SODD polypeptides or polynucleotides, small molecules inhibitors of SODD, etc. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for biasing therapeutic options for treating a tumor, said method comprising the steps of:
   (a) in a sample of a tumor comprising an amount of a SODD gene or gene product, determining the amount of SODD gene or gene product present in the sample, wherein the amount of SODD gene or gene product present in the sample provides a criterion for biasing therapeutic options for treating the tumor; and
   (b) biasing therapeutic options for treating the tumor based on the amount of the SODD gene or gene product present in the tumor sample.

2. A method according to claim 1, wherein the SODD gene or gene product is a SODD gene.

3. A method according to claim 1, wherein the SODD gene or gene product is a SODD gene transcript.

4. A method according to claim 1, wherein the SODD gene or gene product is a SODD polypeptide.

5. A method according to claim 1, wherein the SODD gene or gene product is a SODD gene and the determining step comprises the step of measuring specific binding of a SODD gene-specific probe or primer to the SODD gene to determine the amount of the SODD gene present in the tumor sample.

6. A method according to claim 1, wherein the SODD gene or gene product is a SODD gene transcript and the determining step comprises the step of measuring specific binding of a SODD gene transcript-specific probe or primer to the SODD gene transcript to determine the amount of the SODD gene transcript present in the tumor sample.

7. A method according to claim 1, wherein the SODD gene or gene product is a SODD polypeptide and the determining step comprises the step of measuring an activity of the SODD polypeptide to determine the amount of the SODD gene product present in the tumor sample.

8. A method according to claim 1, wherein the SODD gene or gene product is a SODD polypeptide and the determining step comprises the step of measuring specific binding of a SODD-specific agent to the SODD polypeptide to determine the amount of the SODD gene product present in the tumor sample.

9. A method according to claim 1, wherein the SODD gene or gene product is a SODD polypeptide and the determining step comprises the step of measuring specific binding of a SODD-specific agent to the SODD polypeptide to determine the amount of the SODD gene product present in the tumor sample, wherein the agent is selected from the igroup consisting of a SODD-specific antibody, T-cell receptor, an antigen binding domain of said antibody or said T-cell receptor, and a TNF receptor DR3 domain.

10. A method according to claim 1, wherein the determining step determines a relatively elevated amount of the SODD gene or gene product present in the tumor sample, as compared with a corresponding normal cancer-free sample, and the biasing step comprises reducing the indicability or advisability of radiation therapy for treating the tumor.

11. A method according to claim 1, wherein the tumor is a breast cancer tumor.

12. A method according to claim 1, wherein the determining step comprises the steps of:
   (i) contacting the tumor sample of a tumor with an agent under conditions wherein the agent specifically binds the SODD gene or SODD gene product thereof; and
   (ii) measuring specific binding of the agent to the SODD gene or gene product to determine the amount of the SODD gene or gene product present in the tumor sample.

13. A method according to claim 12, wherein the SODD gene or gene product is a SODD gene and the agent is a probe or primer.

14. A method according to claim 12, wherein the SODD gene or gene product is a SODD gene transcript and the agent is a probe or primer.

15. A method according to claim 12, wherein the SODD gene or gene product is a SODD polypeptide and the agent comprises a component selected from the group consisting of a SODD-specific antibody, T-cell receptor, an antigen binding domain of said antibody or said T-cell receptor, and a TNF receptor DR3 domain.

16. A method according to claim 12, wherein the measuring step determines a relatively elevated amount of the SODD gene or gene product present in the tumor sample, as compared with a corresponding normal cancer-free sample, and the biasing step comprises reducing the indicability or advisability of radiation therapy for treating the tumor.

17. A method according to claim 12, wherein the tumor is a breast cancer tumor.

* * * * *